(12) United States Patent
Nordhoff et al.

(10) Patent No.: US 7,803,969 B2
(45) Date of Patent: Sep. 28, 2010

(54) CONTINUOUS PROCESS FOR THE PRODUCTION AND PURIFICATION OF ACRYLIC ACID

(75) Inventors: Stefan Nordhoff, Recklinghausen (DE); Axel Kobus, Bochum (DE); Stefan Gross, Langenselbold (DE); Hans-Rolf Lausch, Alzenau (DE); Torsten Balduf, Marl (DE); Roland Fornika, Marl (DE); Guenther Bub, Marl (DE)

(73) Assignee: Evonik Stockhausen GmbH, Krefeld (DE)

( * ) Notice: Subject to any disclaimer, the term of this patent is extended or adjusted under 35 U.S.C. 154(b) by 7 days.

(21) Appl. No.: 10/466,176

(22) PCT Filed: Jan. 14, 2002

(86) PCT No.: PCT/EP02/00266
§ 371 (c)(1),
(2), (4) Date: Jan. 5, 2004

(87) PCT Pub. No.: WO02/055469
PCT Pub. Date: Jul. 18, 2002

(65) Prior Publication Data
US 2004/0116741 A1 Jun. 17, 2004

(30) Foreign Application Priority Data
Jan. 12, 2001 (DE) ............... 101 01 160
Oct. 6, 2001 (DE) ............... 101 49 353

(51) Int. Cl.
*C07C 51/42* (2006.01)
(52) U.S. Cl. .................................... 562/600
(58) Field of Classification Search ......... 562/598, 562/600, 523, 531, 532
See application file for complete search history.

(56) References Cited

U.S. PATENT DOCUMENTS

| 3,361,695 A | | 1/1968 | Wolf et al. | |
|---|---|---|---|---|
| 4,780,568 A | * | 10/1988 | Pascoe | 562/599 |
| 5,504,247 A | * | 4/1996 | Saxer et al. | 562/600 |

(Continued)

FOREIGN PATENT DOCUMENTS

DE 197 40 252 3/1999

(Continued)

OTHER PUBLICATIONS

'Crystallization and Precipitation' in Ullmann's Encyclopedia of Industrial Chemistry, Copyright © 2009 by John Wiley & Sons, Inc.*

*Primary Examiner*—Karl J Puttlitz
(74) *Attorney, Agent, or Firm*—Smith Moore Leatherwood LLP

(57) ABSTRACT

The invention relates to a process for the purification of (meth)acrylic acid in a process stage that comprises the following process steps: a) (meth)acrylic acid is crystallized out from a mother liquor; b) crystallized (meth)acrylic acid is separated from the mother liquor; c) at least part of the separated (meth)acrylic acid crystals are melted; d) the melted part is at least partially recycled to the step a) or step b). The process according to the invention, the apparatus suitable for implementing the process, and the use of the apparatus according to the invention for the production of (meth)acrylic acid are characterized by a high purity of the thereby obtainable (meth)acrylic acid as well as by a high efficiency with regard to the achievable yield and necessary energy requirement.

7 Claims, 5 Drawing Sheets

U.S. PATENT DOCUMENTS

| | | |
|---|---|---|
| 6,380,427 B1 * | 4/2002 | Miyazaki et al. ............ 562/600 |
| 7,112,695 B2 * | 9/2006 | Eck et al. .................... 562/600 |
| 2002/0087029 A1 * | 7/2002 | Eck et al. .................... 562/600 |
| 2003/0175159 A1 | 9/2003 | Heilek et al. |

FOREIGN PATENT DOCUMENTS

| | | |
|---|---|---|
| DE | 198 33 049 | 1/2000 |
| EP | 0 675 100 | 10/1995 |
| JP | 07-082210 | 3/1995 |
| JP | 2003-530376 | 10/2003 |
| WO | 01/77056 | 10/2001 |
| WO | 01 77056 | 10/2001 |

\* cited by examiner

CONTINUOUS PROCESS FOR THE PRODUCTION AND PURIFICATION OF ACRYLIC ACID

The present invention relates to a process for the production of very pure (meth)acrylic acid, an apparatus for the production of very pure (meth)acrylic acid, (meth)acrylic acid obtainable by this process, the use of (meth)acrylic acid and substances containing the latter, as well as the use of the apparatus for the production of (meth)acrylic acid. More specifically the process consists of two process steps that comprise in particular the crystallisation and washing of the crystallised (meth)acrylic acid.

"(Meth)acrylic acid" is used in the present text to denote the compounds with the nomenclature names "methacrylic acid" and "acrylic acid". Of the two compounds, acrylic acid is preferred.

It is frequently desired to work up (meth)acrylic acid to purities of up to >99.9 wt. % for its use in polymers. For example in the hygiene sector, in the case of superabsorbers based on polyacrylates, certain byproducts may be present only below the detection limit.

Crystallisation may be mentioned as an alternative to the production of highly pure organic substances. Technically two processes may be used in particular in this connection, namely suspension crystallisation and layer crystallisation (Wintermantel et al., Chem. Ing. Tech. 1991, 63, 881-891; Steiner et al., Chem. Ing. Tech. 1985, 57, 91-102).

Often however a crystallisation by itself is not sufficient in order to remove byproducts sufficiently well from the crystals, since microinclusions of mother liquors or the incorporation of impurities at crystal imperfections, etc., cannot be excluded under finite crystal growth conditions.

Also, the adherence of mother liquor on the crystal can adversely affect the purity of the products.

For this reason the crystals that are formed are often washed with wash liquids after the separation from the mother liquor and/or the crystals are subjected to a sweating process in which impurities of all types may be stripped off. Such a process may be carried out continuously in so-called wash columns. The dissertation of Poschmann (Concerning suspension crystallisation of organic melts and post-treatment of crystals by sweating and washing, Diss. Uni. Bremen, Shaker Verlag, Aachen 1996) provides an overview of such processes.

EP0616998 discloses a process for the production of >99.9 wt. % acrylic acid starting from previously purified product with an acrylic acid content of 97.771 wt. %. The purification effect is achieved by a co-operation of dynamic and static crystallisation processes. A so-called falling film crystallisation is employed here as final crystallisation stage. The operation of such a unit is possible only in a batchwise manner and, due to the many process cycles that are necessary in order to obtain the corresponding purities, involves a high apparatus and logistical effort and a comparatively high energy expenditure.

From WO99/14181 it is known to crystallise crude (meth) acrylic acid for purification in a first step and to work up the product in a second step, optionally by means of wash columns. The process disclosed there starts directly from the condensation products of the catalytic gas phase oxidation for the production of (meth)acrylic acid. This process describes the recycling of the mother liquor formed after the washing and separation of the crystals, to the condensation stage. A product with a purity of 98.8816 wt. % is obtained from 90.972 wt. % acrylic acid by means of this process. This is however not sufficient for many industrial applications. Thus, the content of inhibitors and aldehydes in particular in the pure (meth)acrylic acid forms a critical quantity which, if exceeded, for example in the downstream polymerisation processes, causes disadvantages.

It has been described by Nienrood et al. that acrylic acid can be efficiently purified by suspension crystallisation and subsequent treatment in an hydraulic wash column (so-called TNO process; Proc. Bremen International Workshop on Industrial Crystallization, Bremen, 1994, edited by: J. Ulrich, pp. 4-11; Purification Potential of Suspension Growth Melt Crystallization, Proc. $4^{th}$ International Workshop on Crystal Growth of Organic Materials, Bremen, 1997, edited by: J. Ulrich, Aachen Shaker Verlag, pp. 139-145). The acrylic acid employed in these investigations was obtained from Aldrich and had a purity of 99.75 wt. %. It could be purified by means of this process to a purity of 99.97 wt. %. However, the use of acrylic acid of lower degrees of purity was not disclosed.

The object of the present invention is generally to overcome, by the provision of suitable technical teaching, the disadvantages arising from the prior art.

The object of the present invention was accordingly to provide a process for the production of highly pure (meth) acrylic acid from an unpurified crude (meth)acrylic acid stream from a process for the production of (meth)acrylic acid. In this connection the process should be ideally applicable on an industrial scale and should therefore be superior from the economic as well as ecological aspects to the processes of the prior art. In particular there should be mentioned in this connection an excellent purification capability, while complying with stringent ecological and economic requirements.

In addition a further object forming the basis of the invention was to make available apparatus for the production of highly pure (meth)acrylic acid that permits a purification of unpurified (meth)acrylic acid to very high degrees of purity with a low energy expenditure and in a problem-free and environmentally friendly operation.

The object of the invention was furthermore to make available a process and an apparatus in which, in the production and in particular in the purification of (meth)acrylic acid, the danger of an uncontrolled polymerisation of (meth)acrylic acid is reduced.

Finally, the object of the invention was to provide a further use of the apparatus for the production of (meth)acrylic acid or one of its components.

These objects are achieved by a process with the features set forth in the claims; by an apparatus with the features according to the specification herein; by (meth)acrylic acid with the features according to the specification herein; by fibres, moulded articles, films, foams, superabsorbent polymers or hygiene articles according to the specification herein; by a use with the features according to the specification herein; and by a use with the features according to the specification herein.

The process according to the invention for the purification of (meth)acrylic acid contains a process stage that comprises the following process steps:

a) (meth)acrylic acid is crystallised out from a mother liquor;

b) crystallised (meth)acrylic acid is separated from the mother liquor;

c) at least part of the separated (meth)acrylic acid crystals are melted; and d) the melted part is returned at least partially to the step a) or to the step b).

By means of this process it is surprisingly, but for all that no less advantageously, possible to obtain highly pure products that are also suitable for use in polymers, for example for the hygiene sector.

The process preferably operates continuously. A wash column is advantageously employed to separate the (meth) acrylic acid from the mother liquor. To this end the wash column has a separating region in which the (meth)acrylic acid crystals are washed. For the successful operation of a wash column it is advantageous if the crystals to be washed are sufficiently hard and have a specific narrow size distribution in order to ensure a corresponding porosity and stability of the packed or non-packed filter bed that is formed. It was not previously known that (meth)acrylic acid even with technical qualities of <99.5 wt. % is capable of forming the required crystal properties. It is therefore this property of (meth)acrylic acid that enables the process according to the invention to operate with a wash column and at the same time to recycle the mother liquor that is formed, at least partially, possibly directly, to the crystallisation without adversely influencing the crystal quality due to accumulation of the byproducts so that the process according to the invention can no longer be successfully carried out. This is in no way anticipated by the prior art.

In addition it is preferred if the process according to the invention is characterised by a crystallisation expenditure (Wellinghoff, Wintermantel, CIT 63 (1991) 9, p. 805 Chap. 3.2.1) of 1 to 4.5, preferably less than 1 to 3.5 and particularly preferably from 1 to 2.5, and moreover most particularly preferably from 1 to 1.5.

The process according to the invention may be carried out with unpurified crude (meth)acrylic acid comprising <99.5 wt. % of (meth)acrylic acid. Preferably the crude (meth) acrylic acid that is used has a purity of 50 wt. % to 95 wt. %, preferably 75 wt. % to 90 wt. % of (meth)acrylic acid.

Most particularly preferably the condensed mixture of a catalytic gas phase oxidation may be used for the production of (meth)acrylic acid directly in step a). For this purpose (meth)acrylic acid is generated in a reactor, is then formed into an aqueous solution in a quench tower, following which the (meth)acrylic acid is distilled in a distillation apparatus. The crude (meth)acrylic acid stream that is thereby formed is fed to the purification apparatus. The process allows the production of very pure (meth)acrylic acid from comparatively unpurified crude (meth)acrylic acid. As a result the distillation step can be performed more smoothly, whereby a premature polymerisation is reduced and the quality of the (meth) acrylic acid is improved.

In the crystallisation there are used as crystallisation methods those that enable the purification process according to the invention to be carried out continuously. Suspension crystallisation is preferably used. This may preferably be carried out in a stirred vessel crystalliser, scraper-type crystalliser, cooling plate crystalliser, crystallising coil, drum crystalliser, tube bundle crystalliser or the like. In particular the crystallisation variants mentioned in WO99/14181 may be used for the said purpose. Those crystallisers that can be operated continuously may in turn be used particularly advantageously for this purpose. These are preferably cooling plate crystallisers or scraper-type coolers (Diss. Poschmann, p. 14). A scraper-type cooler is most particularly preferred for the crystallisation.

In principle any wash column that permits the continuous operation of the purification process according to the invention may be used for the process forming the subject matter of the invention. In a customary embodiment the suspension is fed to the upper part of an hydraulic wash column; the liquid phase (mother liquor) is withdrawn via a filter from the column, a tightly packed crystal bed thereby being formed. The liquid phase flows through the crystal bed in the direction of the floor of the column and is forced downwards by the resistance to the flow. A moving, preferably rotating scraper-type device or scraper is located on the floor of the column and in turn produces a suspension from the tightly packed crystal bed and the wash melt introduced in the lower part of the wash column. This suspension is preferably pumped and melted by a heat exchanger. Part of the melt may serve for example as wash melt; this is then pumped back into the column and preferably washes out the crystal bed migrating in the opposite direction, i.e. the crystallised (meth)acrylic acid is washed in countercurrent to the recycled (meth)acrylic acid. The wash melt on the one hand washes the crystals, and on the other hand the melt at least partially crystallises out on the crystals. The released enthalpy of crystallisation heats up the crystal bed in the wash region of the column. In this way a purification effect analogous to the sweating of the crystals is achieved. A purification is produced on the one hand by the washing of the surface of the (meth)acrylic acid crystals with molten—and thus already purified—(meth)acrylic acid, and on the other hand a healing or sweating out of impurities is achieved by the crystallisation of the molten, purified (meth) acrylic acid on the already existing (meth)acrylic acid crystals. This permits the production of highly pure (meth)acrylic acid.

In a special modification of the process according to the invention the recycle stream formed from the recycling of the molten (meth)acrylic acid from step c) to step a) or to step b) is larger than a feed stream that is continuously added externally to step a).

In particular the recycle stream is at least twice, and preferably at least ten times as large as the feed stream. Due to the large recycle stream it is ensured that the thermal load of the (meth)acrylic acid on the heater is reduced.

In order to seed the (meth)acrylic acid to be crystallised, it is advantageous to feed the separated, crystallised (meth) acrylic acid from step b) at least partially to step a). The recycled (meth)acrylic acid crystals facilitate the crystal growth in step a) and thereby assist the separation of the (meth)acrylic acid from the mother liquor.

On account of energy considerations a one-stage purification process with only one process step is in principle especially advantageous and thus particularly preferred. However, depending on the circumstances a two-stage purification process is appropriate.

In order to improve the yield it is expedient to recycle the mother liquor separated after step b) at least partially to step a). (Meth)acrylic acid remaining in the mother liquor may thus be crystallised out further by employing suitable spatial temperature profiles, preferably up to the thermodynamic limit (eutectic).

In an advantageous group of modifications the process according to the invention comprises at least two process stages that in each case involve the steps a) to d), wherein at least one of the following features ($\alpha 1$) to ($\alpha 4$) is met:

($\alpha 1$) separated (meth)acrylic acid, i.e. in this case in particular crystalline and/or molten (meth)acrylic acid from a first process stage is fed at least partially to a second process stage;

($\alpha 2$) separated (meth)acrylic acid, i.e. in this case in particular crystalline and/or molten (meth)acrylic acid from a second process stage is fed at least partially to a first process stage;

($\alpha 3$) mother liquor, i.e. in particular mother liquor separated after the step b), from a first process stage is fed at least partially to a second process stage;

(α4) mother liquor, i.e. in particular mother liquor separated after the step b), from a second process stage is fed at least partially to a first process stage.

Of this group of preferred modifications with at least one of the features (α1) to (α4) of the invention, those modifications are preferred in which at least one of the following features (β1) to (β6) is met:

(β1) crystalline (meth)acrylic acid from the first process stage is fed to at least one of the steps a) and b) of the second process stage;

(β2) molten (meth)acrylic acid from the first process stage is fed to at least one of the steps a) and b) of the second process stage;

(β3) crystalline (meth)acrylic acid from the second process stage is fed to at least one of the steps a), b) and c) of the first process stage;

(β4) molten (meth)acrylic acid from the second process stage is fed at least to one of the steps a), b) and c) of the first process stage;

(β5) the mother liquor of the first process stage separated after the step b) is fed at least partially to the step a) of the second process stage;

(β6) the mother liquor of the second process stage separated after the step b) is fed at least partially to the step a) of the first process stage.

Of this group of preferred modifications of the invention, in the case where the second or further process stage effects an additional purification of the (meth)acrylic acid, i.e. (meth)acrylic acid already purified in a first process stage is purified further in a second (further) process stage, the following embodiments are particularly preferred:

(1) in order to achieve a high purity of the (meth)acrylic acid, molten (meth)acrylic acid from the first process stage is fed to the step a) of the second process stage;

(2) in order to achieve a high purity of the (meth)acrylic acid, crystalline (meth)acrylic acid from the first process stage is fed to the step a) of the second process stage;

(3) in order to permit a thorough washing of the (meth)acrylic acid crystals of the first stage, molten (meth)acrylic acid from the second process stage is fed to the step b) of the first process stage; or (4) in order to make available particularly pure seeding crystals, crystalline (meth)acrylic acid from the second process stage is fed to the step a) of the first process stage.

In this connection a combination of the embodiments (1) and/or (2) and (3) is most particularly preferred.

Of the group of preferred embodiments of the invention, in the case where the second process stage serves to increase the yield, the following embodiments are particularly preferred:

(1) crystalline (meth)acrylic acid from the first process stage is fed as seeding crystals for the crystallisation to the step a) of the second process stage;

(2) in order to increase the yield the mother liquor of the first process stage separated after step b) is fed at least partially to the step a) of the second process stage;

(3) in order to improve the purity molten (meth)acrylic acid from the second process stage is fed to the step a) of the first process stage; or (4) in order to minimise the energy expenditure crystalline (meth)acrylic acid from the second process stage is fed to the step a) of the first process stage.

In this connection a combination of the embodiments (2) and (4) is most particularly preferred.

Advantageously at least two process stages in series are provided. In series may refer both to the separated (meth) acrylic acid, i.e. to the crystalline or to the molten (meth) acrylic acid, as well as to the separated mother liquor.

It is also advantageous to interconnect at least two process stages. In this way the number of melters required for the melting and that are operated in an energy-consuming manner as heat exchangers or heaters is less than the number of stages. For example, a simple interconnection of two process stages can result in the saving of a melter. In this way the operation can be carried out in a significantly more cost-effective manner for the same yield and same purity.

The number of the process stages is governed by the purity and economy to be achieved by the process. In principle the achievable purity of (meth)acrylic acid is restricted by the thermodynamic limit (e.g. eutectic) for a crystallisability of (meth)acrylic acid from the mother liquor.

A special modification of the process according to the invention is characterised by the following features (γ1) and (γ2):

(γ1) crystallisation of (meth)acrylic acid from an unpurified crude (meth)acrylic acid stream from a process for the production of (meth)acrylic acid;

(γ2) separation of the (meth)acrylic acid crystals from the mother liquor by means of a wash column, wherein the mother liquor from step (γ2) is at least partially recycled to the step (γ1), the crude (meth)acrylic acid stream having a purity of <99.5 wt. % of (meth)acrylic acid.

The apparatus according to the invention for the production of (meth)acrylic acid comprises, as fluid-conducting components connected to one another, a (meth)acrylic acid reactor, a quench tower, a distillation apparatus and a purification apparatus, wherein the purification apparatus comprises an apparatus unit having the features (δ1) to (δ4):

(δ1) the apparatus unit comprises a crystallisation region, a separating region, a melter, and at least three feedlines;

(δ2) the crystallisation region is connected to the separating region by a first feedline;

(δ3) the separating region is connected to the melter via a second feedline;

(δ4) the melter is connected to the crystallisation region via a third feedline or to the separating region via a fourth feedline.

The term "fluid-conducting" is understood within the context of the invention to mean that gases or liquids or their mixtures are fed through corresponding lines. For this, there may be used in particular pipelines, pumps and the like.

An apparatus for the production of acrylic acid preferably has the following construction in the region comprising a (meth)acrylic acid reactor and a quench tower, in the synthesis of acrylic acid: propylene and optionally further inert gases such as nitrogen or combustion gases such as $CO_2$ or nitrogen oxides are fed to a first reactor for a first catalytic oxidation via an educt feed that terminates in the first reactor. The first reactor is connected via a further line to a second reactor into which the product of the first catalytic oxidation from the first reactor is introduced for a second catalytic oxidation. The product of the second catalytic oxidation containing acrylic acid is fed via a line located between the second reactor and the quench tower to the lower half of the said quench tower. In the quench tower the product of the second catalytic oxidation is brought into contact with water, the water being fed in above the feedline of the product of the second catalytic oxidation. On the one hand a first phase containing acrylic acid and water is discharged underneath the feedline of the product of the second catalytic oxidation, from the quench tower. This first phase may be at least partially recycled again above the feedline of the product of the second catalytic oxidation, to the quench tower. The first phase not recycled to the quench tower is fed to the distillation apparatus in order for example to undergo an azeotropic separation in which the acrylic acid is concentrated and purified. A second phase containing acrylic acid and water may be removed from the quench tower, above the recycle line of the first phase and below the line for feeding water into the quench tower. This second phase may be fed exactly like the first phase of the distillation apparatus in order for example to undergo an azeotropic separation in which the acrylic acid is concentrated and purified. The waste gases discharged from the quench tower may be fed to a catalytic combustion unit. The combustion gases of the catalytic combustion may be fed as inert gases to the first reactor. The water recovered in the concentration of acrylic acid may be recycled to the quench tower. Further details concerning the production of acrylic acid are disclosed in DE 197 40 252 A1, the contents of which are included here as part of this disclosure.

An apparatus for the production of methacrylic acid comprises the (meth)acrylic acid reactor and a quench tower in the synthesis of methacrylic acid by catalytic gas phase reaction of C4 starting compounds with oxygen. Methacrylic acid may particularly preferably be obtained by catalytic gas phase oxidation of isobutene, isobutane, tert.-butanol, iso-butyraldehyde, methacrolein or methyl tert.-butyl ether. Further details of the production of acrylic acid are disclosed in EP 0 092 097 B1, EP 0 058 927 and EP 0 0608 838, the contents of which are included here as part of this disclosure.

The purification apparatus is able to produce very pure (meth)acrylic acid with degrees of purity of above 99.5 wt. % from a comparatively unpurified crude (meth)acrylic acid stream of around 85 wt. % (meth)acrylic acid. According to the invention it is possible to purify efficiently unpurified crude (meth)acrylic acid streams containing 50 wt. % to 95 wt. % of (meth)acrylic acid, preferably 75 wt. % to 90 wt. % (meth)acrylic acid. This effective purification enables the preliminary purification of the crude (meth)acrylic acid stream with the aid of the distillation apparatus to be reduced, whereby the thermal load of the (meth)acrylic acid is reduced. In this way the quality of the (meth)acrylic acid is improved.

In order to raise the purity of the (meth)acrylic acid still further, the apparatus unit comprises a separate purification apparatus. This separate purification apparatus may be used both for the further purification of the end product as well as for the further purification of the (meth)acrylic acid leaving the melter.

In order to achieve an improved crystallisation the separating region is preferably connected to the crystallisation region by a first recycle line for separated (meth)acrylic acid.

In order to increase the yield the separating region is advantageously connected to the crystallisation region by a second recycle line for separated mother liquor.

In principle, on account of energy considerations a one-stage purification apparatus with only one apparatus unit is particularly advantageous and is therefore particularly preferred. Depending on the circumstances however, a two-stage purification apparatus is appropriate.

In order to improve the effectiveness of the purification, in particular to improve the purity and yield, the apparatus according to the invention contains at least two apparatus units according to the features ($\delta$1) to ($\delta$4), which are joined by at least one connection line, wherein the connection line is an inflow line or a recycle line, and wherein at least one of the following features ($\epsilon$1) to ($\epsilon$4) is met:

($\epsilon$1) the separating region of a first apparatus unit is connected via the connection line to the crystallisation region of a second apparatus unit;

($\epsilon$2) the melter of a first apparatus unit is connected via the connection line to the crystallisation region of a second apparatus unit;

($\epsilon$3) the separating region of a second apparatus unit is connected via the connection line to the crystallisation region of a first apparatus unit;

($\epsilon$4) the melter of a second apparatus unit is connected via the connection line to the crystallisation region of a first apparatus unit.

The connection lines may be inflow lines as well as recycle lines.

For example, it is expedient corresponding to the process according to the invention to provide an inflow line to the crystallisation region of the second apparatus unit (second process stage) in order to increase the yield from the separating region of the first apparatus unit (first process stage). A recycle line between the separating region of the second stage and the crystallisation region of the first stage is however convenient for supplying seeding crystals.

In this way it is possible in an advantageous manner to provide a sequence of at least two apparatus units in order to improve the purity and the yield.

By interconnecting at least two apparatus units the number of necessary melters can be reduced and in this way the energy consumption for the operation of the apparatus can be lowered.

In the process according to the invention for the purification of acrylic acid, a temperature in the range from $-20°$ C. to $20°$ C., preferably from $-10°$ C. to $13°$ C. and a pressure of 1 to 10 bar are adjusted in the separating region. It is preferred to set a lower temperature and a lower pressure in the lower section of the separating region than in the upper section of the separating region. Preferably a temperature of $-20°$ C. to $<12°$ C. and a pressure of 1 to 2 bar are established in the lower section of the separating region. A temperature of at least $12°$ C. and a pressure of 1 to 10 bar, preferably 3 to 7 bar, are established in the upper section of the separating region.

In the process according to the invention for the purification of acrylic acid, a temperature in the range from $-20°$ C. to $20°$ C., preferably from $-12°$ C. to $13°$ C. and a pressure of 0.5 to 10 bar, preferably 0.8 to 2 bar, are established in the crystallisation region.

In the process according to the invention for the purification of acrylic acid, a temperature in the range from $10°$ C. to $50°$ C., preferably from $11°$ C. to $30°$ C. and a pressure of 1 to 10 bar, preferably 3 to 7 bar, are established in the melter.

In the process according to the invention for the purification of methacrylic acid, a temperature in the range from $-5°$ C. to $30°$ C., preferably from $-3°$ C. to $20°$ C. and a pressure of 1 to 10 bar are established in the separating region. It is preferred that a lower temperature and a lower pressure are set in the lower section of the separating region than in the upper section of the separating region. Preferably a temperature of $-16°$ C. to $<15°$ C. and a pressure of 1 to 2 bar are established in the lower section of the separating region. A temperature of at least $15°$ C. and a pressure of 1 to 10 bar are established in the upper section of the separating region.

In the process according to the invention for the purification of acrylic acid, a temperature in the range from $-5°$ C. to $30°$ C., preferably from $-3°$ C. to $20°$ C. and a pressure of 1 to 10 bar, preferably 1 to 2 bar, are established in the crystallisation region.

In the process according to the invention for the purification of acrylic acid, a temperature in the range from $10°$ C. to $50°$ C., preferably from $11°$ C. to $30°$ C. and a pressure of 1 to 10 bar, preferably 3 to 7 bar, are established in the melter.

Temperature and pressure relationships that permit a reliable and fault-free transportation of the (meth)acrylic acid and the substances optionally accompanying the latter are established in the feedlines.

The process according to the invention enables a relatively unpurified (meth)acrylic acid to be used as starting material, whereby the preliminary expenditure on a distillation of the (meth)acrylic acid obtained from the synthesis is reduced. In this way the thermal load of the (meth)acrylic acid, which can lead to undesired polymerisations, is in particular reduced.

The fibres, moulded articles, films, foams, superabsorbent polymers or hygiene articles according to the invention are at least based on or at least contain the (meth)acrylic acid according to the invention.

The (meth)acrylic acid according to the invention is used according to the invention in or for the production of fibres, moulded articles, films, foams, superabsorbent polymers or hygiene articles.

The apparatus according to the invention or the purification apparatus according to the invention or the process according to the invention is used according to the invention for the production of acrylic acid that has a purity of more than 90 wt. %, preferably more than 95 wt. % and particularly preferably more than 99.5 wt. %, referred in each case to the (meth) acrylic acid with impurities.

The purification process according to the invention or the process according to the invention is preferably used for the production of methacrylic acid that has a purity of more than 90 wt. %, preferably more than 95 wt. % and particularly preferably more than 99.5 wt. %, in each case referred to the (meth)acrylic acid with impurities.

In a special modification of the process according to the invention for the purification of (meth)acrylic acid, the process comprises two process steps:
 γ1) crystallisation of (meth)acrylic acid from an unpurified crude (meth)acrylic acid stream from a process for the production of (meth)acrylic acid;
 γ1) separation of the (meth)acrylic acid crystals from the mother liquor by means of a wash column, the mother liquor from step γ2) being at least partially recycled to the step γ1), wherein the crude (meth)acrylic acid stream preferably has a purity of <99.5 wt. % of (meth)acrylic acid.

A mechanically operated wash column (Diss. Poschmann, p. 18) is also and primarily suitable for the invention. In a mechanical wash column—reference is made for example to EP 0 193 226 B and NL 1007687 A—a compact crystal bed is produced within the column by means of a piston permeable to the melt. The piston may be situated at the upper or lower end of the column; in the first case the feed of the suspension takes place in the upper region of the column, and in the second case in the middle or lower region. The piston is permeable to the melt, so that on compression melt leaves at the rear side of the piston, where it is withdrawn. In a similar way to an hydraulic wash column, the mechanical wash column also contains a scraper device, for example a moving, preferably rotating scraper, in order to scrape off crystals from the crystal bed and to convert them with the wash melt into a suspension. The wash melt moves in countercurrent to the crystal bed. Suspension is withdrawn from the side of the wash column opposite the piston, and after the melting stage a part of the melt can be recycled as wash melt and the other part can be removed as highly pure product from the circulation.

Embodiments of suspension crystallisation with downstream washing of the crystals in an hydraulic or mechanical wash column are described in the book "Melt Crystallisation Technology" by G. F. Arkenbout, Technomic Publishing Co. Inc., Lancaster-Basel (1995), pp. 265-288 as well as in the article on the Niro freeze concentration method for waste water preconcentration in Chemie Ingenieur Technik (72) (10/2000), 1231-1233.

Depending on the intended use, a conventional wash liquid known to the person skilled in the art may be used as wash liquid (in aqueous solutions, for example water). As already indicated, a partial amount of the molten crystals themselves is most particularly preferred for washing the crystallised (meth)acrylic acid. By this measure it is on the one hand ensured that for the production of highly pure products no further substances have to be introduced in the system, and on the other hand the molten crystals also serve to force back the mother liquor front in the wash column and exert at the same time a cleaning effect on the crystals that is similar to sweating. There is no product loss since the wash liquid in turn crystallises out on the crystals to be washed and is thus recovered in the product (e.g. prospectus published by Niro Process Technology B.V., Crystallisation and wash column separation set new standards in purity of chemical compounds).

In a modification of the process according to the invention the separated, in particular crystalline and/or molten (meth) acrylic acid is purified in a separate purification process. For example it is possible to treat the mother liquor from step b) at least once by means of a further purification process before it is recycled to step a). Such processes are well known to the person skilled in the art. The following in particular are preferably used as such processes:

1.) Simple Distillation

Separation into low boiling point compounds (acetic acid, water, etc.), medium boiling point compounds ((meth)acrylic acid) and high boiling point compounds (MSA, PTA, etc.). The purification of unpurified (meth)acrylic acid (in particular from water and acetic acid) is carried out in the majority of cases by means of azeotropic rectification. Entrainment agents such as toluene or MIBK may for example be used (EP 0 695 736 B1).

2.) Extraction of Acrylic Acid (Meth)acrylic acid can be obtained by extraction with n-butanol. An aqueous phase remains in which the subsidiary components are dissolved. The extraction of (meth)acrylic acid from unpurified solutions belongs, like distillation, to the prior art.

(Meth)acrylic acid may for example also be extracted from aqueous solutions with liquid ion exchangers, mixtures of tri-n-alkylamines and aliphatic alcohols or n-butanol (Vogel et al., Chem. Eng. Technol. 23 (2000)1, pp. 70-74; Tamada et al.: in Solvent Extraction 1990, Ed.: T. Sekine, Elsevier Science Publishers B.V., pp. 1791-1796; JP 57 095 938; WO 98/40342; Information brochure from SULZER Chemtech on fractional extraction of (meth)acrylic acid with n-butanol).

3.) Dewatering of (Meth)Acrylic Acid by Pervaporation
DE 4401405 A1

Advantageously the mother liquor from step b) can, before being recycled to step a), be treated at least once by a process including the steps a) and b) and the in each case purer branched-off partial stream can be recycled to step a) of the initial process or a preceding process in order thereby to achieve a maximum degree of purity with minimal loss of yield.

FIG. 2 illustrates this state of affairs. The mother liquor from the crystal separation in the wash column may likewise be treated in a following crystallisation vessel. The suspension that is formed may then in turn be worked up as is customary in a wash column. The mother liquor that is now formed may be treated in a similar way in subsequent stages. In this connection one may either recycle the in each case purer partial streams formed by this procedure to the crystallisation of the first purification process, or alternatively to the crystallisation of a previous process. In this way the maximum purity with a minimum amount of waste may be achieved with a relatively low expenditure on apparatus.

The processes according to the invention may be carried out continuously as well as batchwise, continuous operation being preferred since such an operation is particularly economical.

In a further modification the invention is concerned with the use of the (meth)acrylic acid produced according to the invention in a process for the production of polymers, preferably superabsorbers, detergents or special polymers for the following sectors: effluent treatment, dispersion paints, cosmetics, textiles, leather finishing and paper manufacture.

The invention also relates to fibres, moulded articles, films, foams, superabsorbent polymers or hygiene articles that are at least based on or contain the aforedescribed (meth)acrylic acid according to the invention.

The invention moreover relates to the use of the aforedescribed (meth)acrylic acid according to the invention according to claim 11 in or for the production of fibres, moulded articles, films, foams, superabsorbent polymers or hygiene articles.

The (meth)acrylic acid according to the invention is advantageously used for the production of polymers, preferably superabsorbers, detergents or special polymers for sectors such as effluent treatment, dispersion paints, cosmetics, textiles, leather finishing and paper manufacture.

Superabsorbent polymers are understood to denote polymers that absorb a multiple of their own weight of water or aqueous liquids. Preferably more than 50% of the superabsorbent polymers are based on acrylic acid as monomers. Further details concerning superabsorbent polymers, their production and use in hygiene articles may be found in "Modern Superabsorbent Polymer Technology", Fredric L. Buchholz, Andrew T. Graham, Wiley-VCH, 1998, the contents of which are included as part of this disclosure.

Furthermore, the combinations of features identified hereinbefore by reference numerals constitute in each case individual embodiments of the present invention.

Further details and advantageous developments are described in more detail hereinafter with the aid of the following drawings, which are intended to illustrate the invention by way of example.

In the drawings:

FIG. 1 shows a process scheme in which the process (one-stage process) is described summarily as follows:

Figure 1:
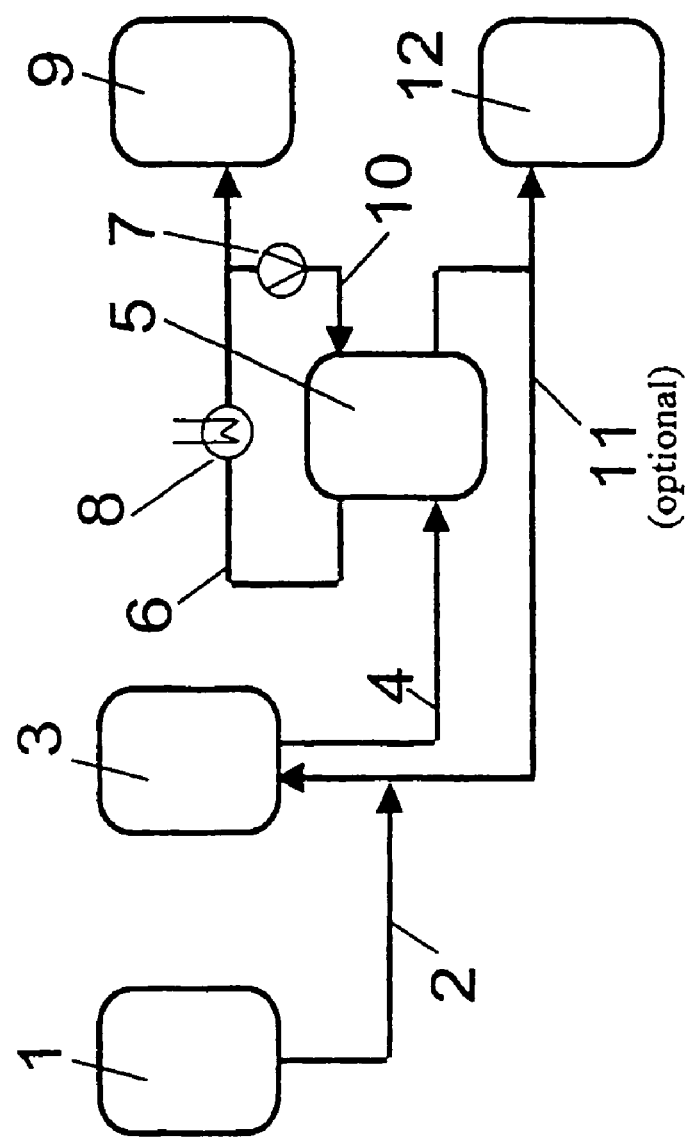
FIG. 1 shows diagrammatically a further process scheme according to the invention according to FIG. 1.

Stage 1:
1. Storage container
2. Feed from 1 to 3
3. Suspension producer (e.g. cooled plate crystalliser, scraper-type cooler)
4. Feed from 3 to 5
5. Hydraulic or mechanical wash column
6. Product circulation
7. Product circulation pump
8. Product circulation heat exchanger
9. Product container
10. Product recycling to the countercurrent wash in wash column 5
11. Mother liquor recycling (optional)
12. Mother liquor container (discharge)

The wash column 5, the suspension producer 3, the product circulation heat exchanger 8, the feed 4, the product circulation 6 and the product recycling 10 correspond respectively to the separating region, crystallisation region, melter, first feedline, second feedline, fourth feedline and, if crystal formation takes place in the wash column, to the third feedline.

The melt to be separated is fed in the liquid state, i.e. temperature controlled to just above equilibrium, from the storage container 1 via the feedline 2 to the suspension producer 3. By cooling the melt below the equilibrium temperature crystals are continuously formed in the suspension producer 3 with a suspension density of between 5% and 50% (preferably 20% to 30%). The suspension is continuously fed via the feedline 4 to the wash column 5, where it is separated into a liquid phase and a solid phase by moving or stationary filters (hydraulic or mechanical filters, see above). The filtrate leaves the wash column 5 and is continuously fed to the mother liquor container 12. In order to increase the yield it is optionally possible to recycle at least part of the filtrate also via the mother liquor recycle line 11 to the suspension producer 3.

The crystals in the wash column 5 are compacted to form a crystal bed and, depending on the type of wash column, are scraped off at the top or bottom with rotating knives. The scraped-off product crystals are pumped as suspension in the product circulation 6 by means of the circulation pump 7 and are melted by the melt enthalpy supplied by the heat exchanger 8.

Part of the circulation is recycled as wash liquid through the product recycle line 10 to the countercurrent wash in the wash column. The other part leaves the apparatus as product and is passed to the container 9.

If in this one-stage procedure product losses due to the discharge cannot be reduced to a minimum, the mother liquor from the first crystallisation stage may optionally be worked up in one or more further crystallisation stages or with different purification means.

Figure 2:
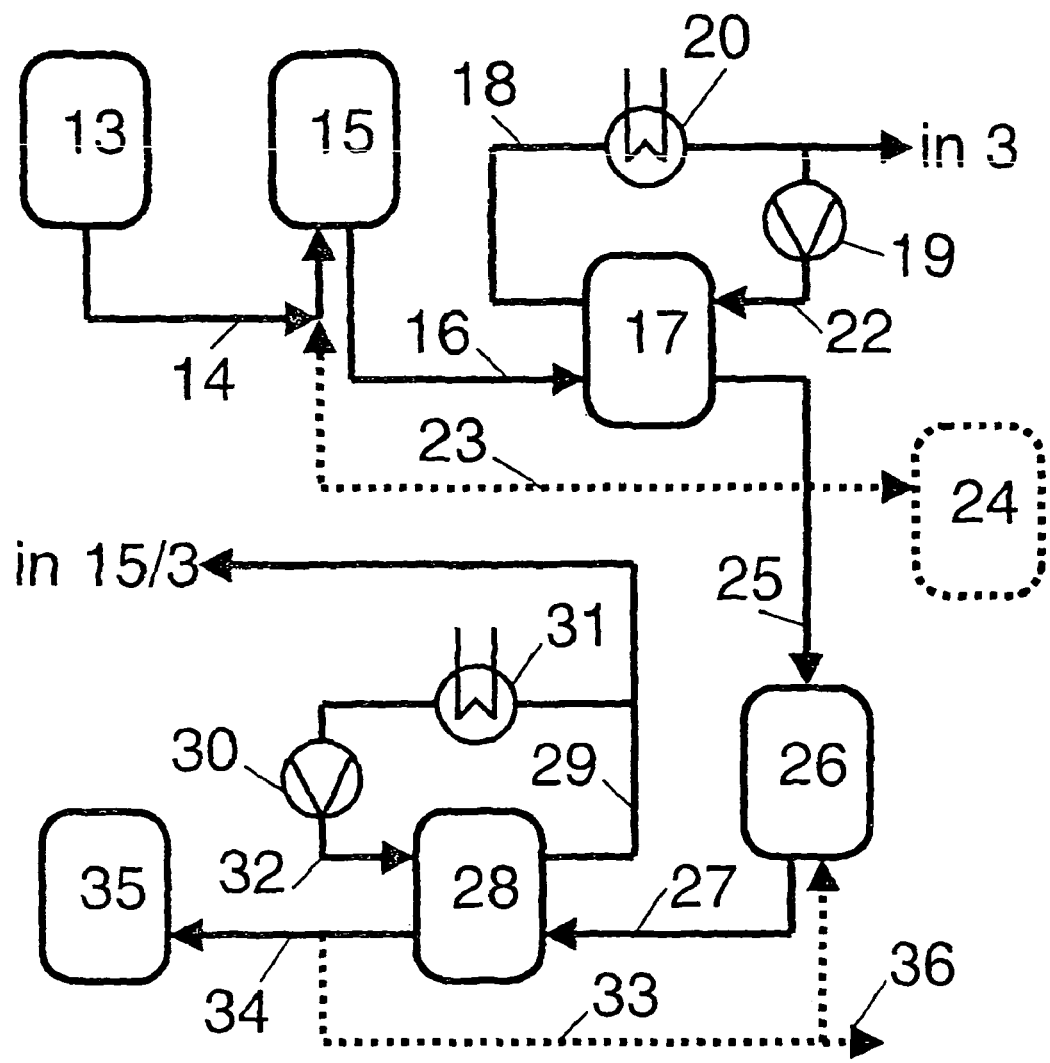
FIG. 2 shows diagrammatically a process scheme according to the invention with two process stages connected in series.

FIG. 2 shows by way of example the implementation of the process in several crystallisation stages Stage 2/3 etc.:
13. Mother liquor container of the first stage (=12)
14. Feed from 13 to 15
15. Stage 2 suspension producer (e.g. cooling plate crystalliser, scraper-type cooler)
16. Feed from 15 to 17
17. Hydraulic or mechanical wash column
18. Product circulation of the second stage
19. Product circulation pump
20. Product circulation heat exchanger
21.
22. Product recycling to 17
23. Mother liquor recycling to the crystalliser of the second stage (optional)

24. Mother liquor container of the second stage (discharge)
25. Mother liquor feed from the second stage to 26
26. Third stage suspension producer (e.g. cooling plate crystalliser, scraper-type cooler)
27. Feedline of the product from 26 to 28
28. Hydraulic or mechanical wash column
29. Product circulation of the third stage
30. Product circulation pump
31. Product circulation heat exchanger
32. Product recycling to 28
33. Mother liquor recycling to the crystalliser of the third stage (optional)
34. Feed from 28 to 35
35. Mother liquor container (discharge) of the third stage
36. Optional feed to further purification stages The suspension producer 15, wash column 17, product circulation heat exchanger 20, feedline 16, product circulation 18, product recycling 22 and mother liquor recycling 23 correspond in each case in the first apparatus unit to the crystallisation region, separating region and melter, first feedline, second feedline, third or fourth feedline, and second recycling.

The suspension producer 26, wash column 28 and the product circulation heat exchanger 31 of the product circulation 32, product recycling 29 and mother liquor recycling 33 correspond in each case in the second apparatus unit to the crystallisation region, separating region, melter, second feedline, third or fourth feedline, and second recycling.

The mother liquor feedline 25 corresponds to a connection line.

The mother liquor (12/13) from the first stage is partially or completely fed to the suspension producer of the second stage 15. By cooling below the equilibrium temperature of the melt, crystals with a suspension density of between 5% and 50% (preferably 20% to 30%) are continuously formed in the suspension producer 15. The suspension is continuously fed via the feedline 16 to the wash column of the second stage (17), where it is separated into a liquid phase and a solid phase by moving or stationary filters (hydraulic or mechanical, see above). The crystals are compacted to form a crystal bed and, depending on the type of wash column 17, are scraped off at the top or bottom by means of rotating knives. The product crystals that are scraped off are optionally (as in the first stage) pumped as suspension in the product circulation 18 by means of the circulation pump 19 and melt due to the melt enthalpy supplied by the heat exchanger 20. Part of the suspension may be recycled (22) as wash liquid to the countercurrent wash in the wash column. The other part may be recycled as molten product to the suspension producer of the first stage (3). The filtrate leaves the wash column 17 and is continuously fed to the mother liquor container 24. In order to improve the yield it is optionally possible to recycle at least part of the filtrate also via the mother liquor recycle line 23 to the suspension producer 15 and/or work it up further in a third stage. For this purpose the mother liquor is fed via 25 to a further suspension producer 26. The suspension obtained as above is led via 27 to the wash column 28, where it is compacted to form a crystal bed and, depending on the type of wash column 28, is scraped off from the top or bottom using rotating knives. The scraped-off product crystals are optionally (as in the first stage) pumped as suspension in the product circulation 29 by means of the circulation pump 30 and melt due to the melt enthalpy supplied by the heat exchanger 31. Part of the suspension may be recycled (32) as wash liquid to the countercurrent wash in the wash column. The other part may be recycled as molten product to the suspension producer of the first stage 3 or to the second stage 15.

Figure 3:
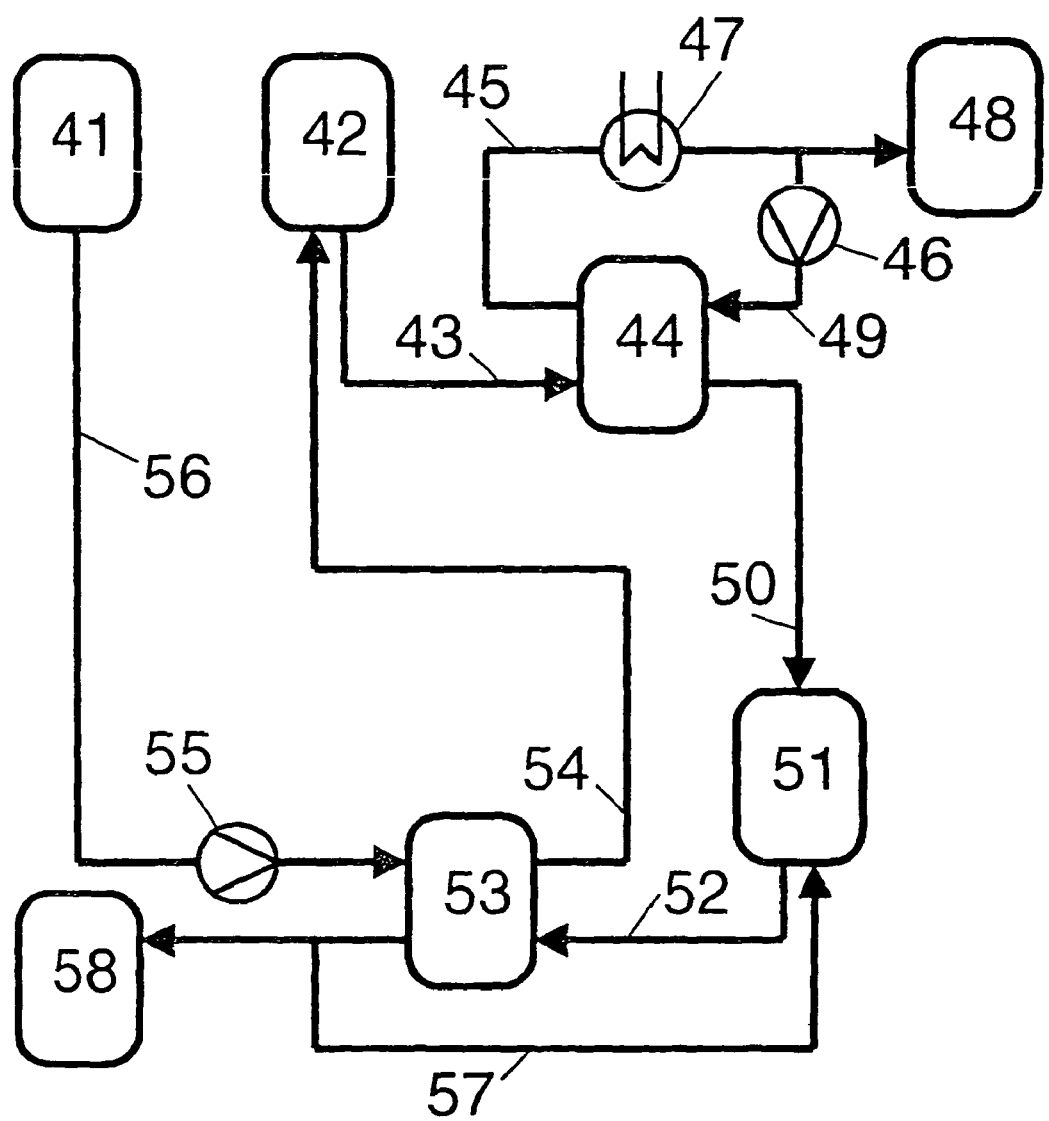
FIG. 3 shows diagrammatically a process scheme according to the invention with two interconnected process stages.

FIG. 3 shows a further preferred arrangement of the working-up process according to the invention.
41. Storage container
42. Suspension producer (e.g. cooling plate crystalliser, scraper-type cooler)
43. Feed from 42 to 44
44. Hydraulic or mechanical wash column
45. Product circulation
46. Product circulation pump
47. Product circulation heat exchanger
48. Product container
49. Product recycling to the countercurrent wash in wash column 44
50. Feed of the second stage=mother liquor from stage 1 (from the wash column 44)
51. Stage 2 suspension producer (e.g. cooling plate crystalliser, scraper-type cooler)
52. Feed from 51 to 53
53. Hydraulic or mechanical wash column
54. Product from the second stage (suspension mixed with the original from 41, which is fed not to stage 1 but to stage 2), which is fed to the scraper-type cooler of the first stage (42)
55. Product feed pump
56. Feedline from the first stage (41) directly to the head of the wash column 53 of the second stage
57. Mother liquor recycling to the crystalliser of the second stage (51) (optional)
58. Mother liquor container of the second stage (discharge)

The suspension producer 42, the wash column 44, the product circulation heat exchanger 47, the product circulation 45, product recycle line 49 and the feed 43 correspond in each case in the first apparatus unit to the crystallisation region, to the separating region and melter, to the second feedline, to the third or fourth feedline, and to the first feedline.

The suspension producer 51, the wash column 53, the feed 52, the mother liquor recycling line 57 correspond in each case in the second apparatus unit to the crystallisation region, to the separating region, to the first feedline and to the second recycle line.

The feedlines 54, 50 correspond to connection lines. The interconnected arrangement illustrated here by way of example advantageously means that the second apparatus unit does not require a melter.

A particularly preferred variant of a two-stage or multi-stage embodiment feeds the melt of the first stage 41 to be separated through the feedline 56 and the pump 55 to the head of the wash column of the second stage 53, where the scraped-off product crystals of the second stage are fed as suspension 54 to the suspension producer of the first stage 42. This variant has the energy advantage of being able to dispense with a melting step in the second stage and the crystals now present in the first stage do not have to be concentrated by freezing out again.

The countercurrent washing in the wash column of the second stage 53 is achieved here by the melt from 41 via the feed 56 of the first stage, which is very pure compared to the impurity concentration in the second stage and thus permits a washing that is similarly effective to a washing with product.

Although a combination of a scraper-type cooler and a wash column is known for the production of organic substances in a high state of purity, it was not foreseeable that this process would also be extremely suitable for concentrating (meth)acrylic acid with initial purities of <99.5 wt. %. With regard to the unknown crystallisation properties of (meth) acrylic acid of lesser purity, it was not to be expected that a concentration of more than 14% could be realised in one stage. It was furthermore surprising that the content of impurities, such as further organic carbon compounds, can be lowered by the process according to the invention to values below the detection limit. In particular critical compounds such as furfural, inhibitors, acetic acid or maleic acid can also be reduced to sub-critical values in this way. This could not have been deduced from the prior art and is also not obvious from the latter.

Figure 4:
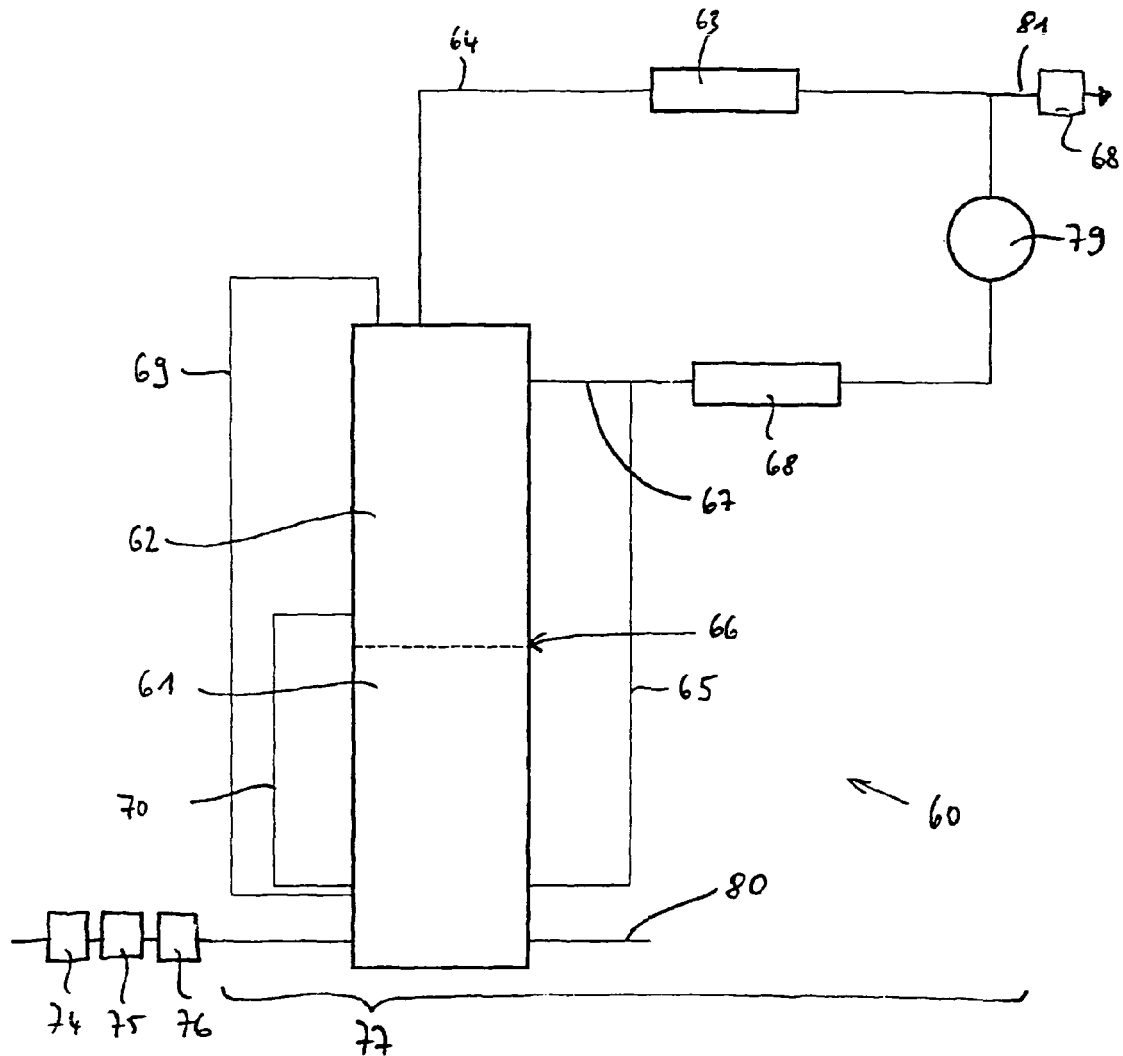
FIG. 4 shows diagrammatically a process scheme according to the invention with one process stage.
Figure 5:
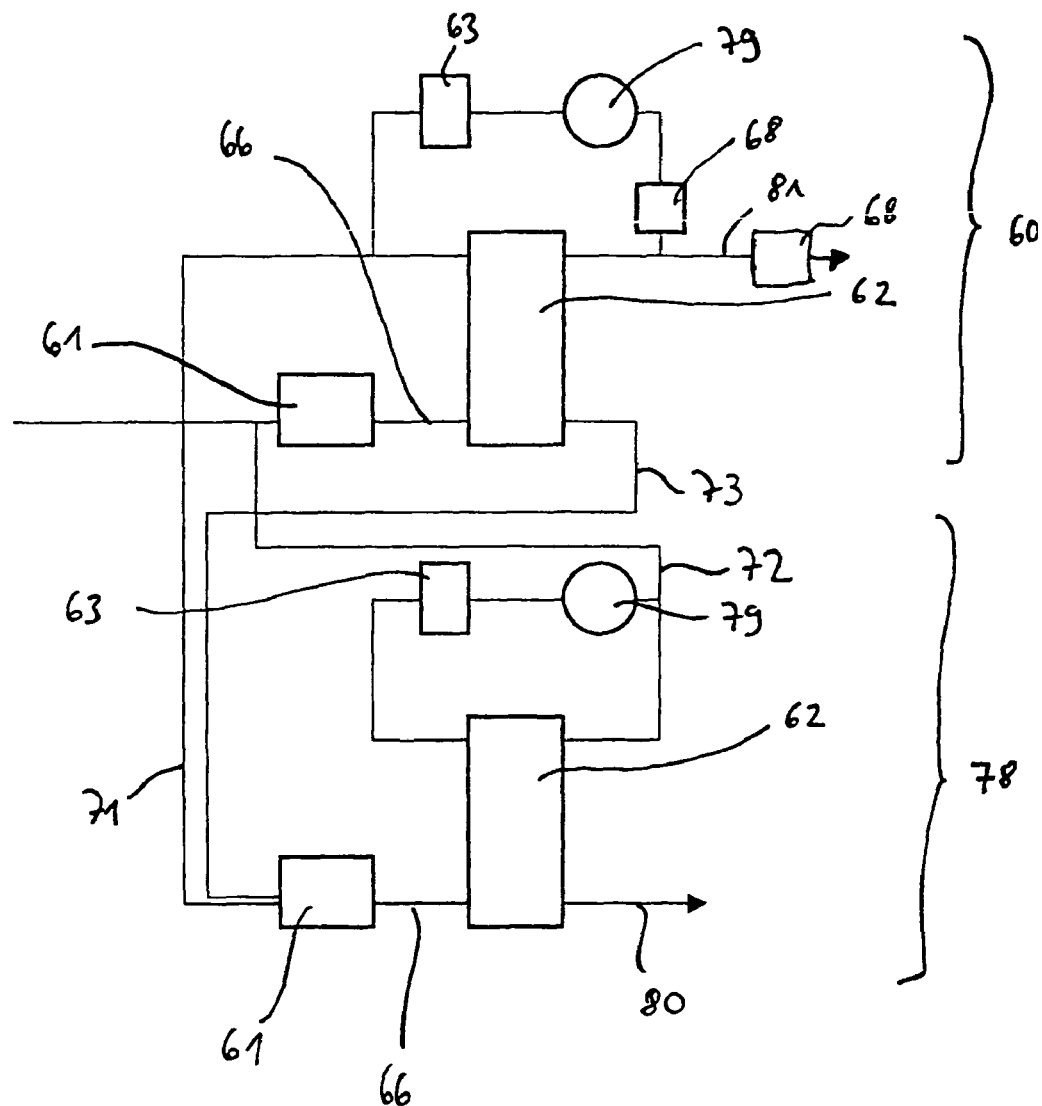
FIG. 5 shows a process scheme according to the invention with two process stages.

FIG. 4 shows a process scheme according to the invention with one process stage, and FIG. 5 shows a process scheme according to the invention with two process stages.

60. Apparatus unit (first process stage)
61. Crystallisation region
62. Separating region
63. Melter
64. Second feedline
65. Third feedline
66. First feedline
67. Fourth feedline
68. Separate purification apparatus
69. First recycle line
70. Second recycle line
71. Connection line
72. Connection line
73. Connection line
74. (Meth)acrylic acid reactor
75. Quench tower
76. Distillation apparatus
77. Purification apparatus
78. Apparatus unit (second process stage)
79. Pump
80. Residual mother liquor outflow
81. Product outflow FIG. 4 shows an apparatus according to the invention for the production of (meth)acrylic acid with a (meth)acrylic acid reactor 74, a quench tower 75, a distillation apparatus 76 and a purification apparatus 77, wherein the purification apparatus 77 contains a crystallisation region 61 and a separating region 62. The crystallisation region 61 and the separating region 62 lie closely adjacent to one another, and preferably the crystallisation region 61 and the separating region 62 are not connected via pipelines but are directly joined to one another. A crystal growth preferably also takes place in a single housing during the washing of the crystals, in particular during the separation of the crystals from the mother liquor. The crystallisation region 61 and the separating region 62 are connected to one another via a first feedline 66, which may be formed by the common housing. The separating region 62 is connected via a second feedline 74 to the melter 63, which melts the (meth)acrylic acid crystals separated in the separating region from the mother liquor. The molten (meth)acrylic acid is conveyed by means of a pump 79 either via a fourth feedline 67 to the separating region 62 or via a third feedline 65 to the crystallisation region 61. A separate purification apparatus 68 advantageously serves to increase the purity of the (meth)acrylic acid. In order to promote the crystallisation in the crystallisation region 61, (meth)acrylic acid crystals separated in the separating region 62 are fed as seeding crystals with the aid of a first recycle line 69 to the crystallisation region 61. The yield is increased, in which connection the (meth)acrylic acid remaining in the mother liquor in the case of an incomplete separation in the separating region 62 is recovered by feeding the mother liquor from the separating region 62 via a second recycle line 70 to the crystallisation region 61. The purified (meth)acrylic acid is removed from the circulation by means of a product outflow line 81. Residual mother liquor that can no longer be utilised is removed by means of a residual mother liquor outflow line 80.

FIG. 5 shows a purification apparatus 77 with two apparatus units 60, 78. The purification apparatus 77 thus involves two process stages. In order to increase the achievable purity of the (meth)acrylic acid as well as the yield, the two apparatus units 60 are connected to one another by connection lines 71, 72, 73.

With regard to the mother liquor that is fed from the first apparatus unit 60 via a connection line 73 to the second apparatus unit 78, the two apparatus units 60 and 78 are connected in series.

In order to promote crystal growth in the second apparatus unit 78, separated (meth)acrylic acid crystals are fed from the separating region 62 of the first apparatus unit 60 via a connection line 71 to the crystallisation region 61 of the second apparatus unit 78. This is particularly expedient in the case where the concentration of the (meth)acrylic acid in the mother liquor fed to the second apparatus unit 78 already lies close to the concentration limiting value for a crystallising out of (meth)acrylic acid from the mother liquor. By means of this measure the yield of the purification apparatus 77 is raised overall.

In order to increase the purity of the (meth)acrylic acid obtained from the second process stage by means of the second apparatus unit 78, which on account of the lower (meth)acrylic acid concentration in the mother liquor that is fed to the second apparatus unit 78, may precipitate out at a lower concentration, the (meth)acrylic acid obtained in the second process stage is fed for further purification, via a connection line 72 to the crystallisation region 61 of the first apparatus unit 60. An improved purity of the obtained (meth)acrylic acid is ensured by this post-purification.

With regard to the transportation of the mother liquor, the first apparatus unit 60 is followed by the second apparatus unit 78. With regard to the transportation of the (meth)acrylic acid, the second apparatus unit 78 is followed by the first apparatus unit 60. In this way the two apparatus units 78 and 60 are interconnected with one another.

The invention is now described in more detail with the aid of non-limiting examples.

EXAMPLES

Embodiments of the Crystallisation of Acrylic Acid and Methacrylic Acid

Acrylic acid having the following composition (Table 1) was added to the scraper cooler of an apparatus corresponding to FIG. 1, comprising a scraper-type crystalliser for producing the suspension and a mechanical wash column with a piston arranged at the bottom and a line arranged at the top for removing purified melt.

TABLE 1

| Name | | Receiver |
|---|---|---|
| Colour No. | — | >700 |
| Water | % | 0.540 |
| Acetic acid | % | 0.061 |
| Furfural | % | 0.052 |
| Benzaldehyde | % | 0.141 |
| Propionic acid | % | 0.049 |
| Acrolein | % | 0.0007 |
| Protoanemonine | % | 0.039 |
| Acrylic acid | % | 93.9 |

TABLE 1-continued

| Name | | Receiver |
|---|---|---|
| MEHQ | % | 0.081 |
| HQ | % | 0.101 |
| PZ | % | 0.161 |
| D-acrylic acid | % | 2.3 |
| MSA | % | 1.52 |
| Miscellaneous | % | 1.06 |

In order to raise the concentration of impurities in the scraper cooler, in addition ca. 8% of water was added at the start. Acrylic acid having the composition shown in Table 2 was used as feed.

TABLE 2

| Name | | Educt |
|---|---|---|
| Colour No. | — | 3 |
| Water | % | 0.27 |
| Acetic acid | % | 0.026 |
| Furfural | % | 0.0119 |
| Benzaldehyde | % | 0.0023 |
| Propionic acid | % | 0.031 |
| Acrolein | % | |
| Protoanemonine | % | 0.0014 |
| Acrylic acid | % | 99.766 |
| MEHQ | % | 0.044 |
| HQ | % | <0.001 |
| PZ | % | <0.0001 |
| D-acrylic acid | % | 0.09 |
| MSA | % | <0.005 |
| Miscellaneous | % | |

The scraper cooler was cooled, and at ca. 5° C. a crystal layer formed in the scraper cooler that was scraped off by the rotating knives in the scraper cooler to form a suspension.

The filtered-off mother liquor was constantly completely recycled to the scraper cooler. All subsidiary components were thus concentrated in the circulation, with the result that during the tests the acrylic acid content in the scraper cooler constantly fell. This was compensated by a continuous drop in the scraper cooler temperature to about 2° C., in order to permit a constant formation of crystals on account of the drop in the equilibrium temperature. After ca. 24 hours' operation the liquid phase in the crystallisers (=filtrate from the wash column) had the composition according to Table 3.

TABLE 3

| Name | | Filtrate |
|---|---|---|
| Colour No. | — | >700 |
| Water | % | 9.08 |
| Acetic acid | % | 0.178 |
| Furfural | % | 0.14 |
| Benzaldehyde | % | 0.18 |
| Acrolein | % | 0.115 |
| Propionic acid | % | 0.0018 |
| Protoanemonine | % | 0.06 |
| Acrylic acid | % | 85.8 |
| MEHQ | % | 0.219 |
| HQ | % | 0.115 |
| PZ | % | 0.167 |
| D-acrylic acid | % | 0.3 |
| MSA | % | 2.1 |
| Miscellaneous | % | 1.56 |

The crystal suspension removed from the crystalliser was compacted in the wash column to form a compact crystal bed. The crystals were scraped off from the top side of the crystal bed by means of a rotating scraper, pumped as a crystal suspension in the product circulation, and melted by the heat exchanger. Part of the suspension was recycled for the countercurrent wash to the crystal bed. The other part was continuously obtained as product. Table 4 gives by way of example the product analysis of the achieved product qualities of the acrylic acid that was taken ca. 1 hour later than the sample from Table 3, i.e. ca. 25 hours after the start of the experiment.

TABLE 4

| Name | | Product |
|---|---|---|
| Colour No. | — | 8 |
| Water | % | 0.019 |
| Acetic acid | % | 0.011 |
| Furfural | % | <0.0001 |
| Benzaldehyde | % | <0.0001 |
| Propionic acid | % | 0.021 |
| Acrolein | % | <0.0001 |
| Protoanemonine | % | <0.0001 |
| Acrylic acid | % | 99.914 |
| MEHQ | % | 0.025* |
| HQ | % | <0.001 |
| PZ | % | <0.0001 |
| D-acrylic acid | % | 0.01 |
| MSA | % | <0.005 |
| Miscellaneous | % | — |

*Product post-stabilised

As can be seen from Table 4, the process according to the invention enables extremely pure acrylic acid to be produced. On average 6 kg/h were produced.

Instead of acrylic acid, methacrylic acid having the composition according to Table 5 was added to the scraper cooler and in addition ca. 2.5% of water was metered in.

TABLE 5

| Name | | Receiver |
|---|---|---|
| Colour No. | — | >700 |
| Water | % | 1.8 |
| Hydroxyisobutyric acid | % | 1.14 |
| Methacrylamide | % | 0.65 |
| Methyl methacrylate | % | 0.21 |
| Methacrylic acid | % | 95.0 |
| Acetic acid | % | 0.16 |
| Isobutyric acid | % | <0.01 |
| Acrylic acid | % | <0.01 |
| Propionic acid | % | 0.01 |
| MEHQ | % | 0.0281 |
| HQ | % | 0.0058 |

Methacrylic acid having the same composition according to Table 5 was used as feedstock for the experiments.

The scraper-type cooler was cooled, the temperature in the scraper-type cooler falling to ca. 9° C. with the formation of a crystal layer that was scraped off by the rotating scrapers in the scraper-type cooler, to form a suspension.

The mother liquor that was filtered off was constantly completely recycled to the scraper-type cooler. All subsidiary components in the circulation were thereby concentrated, with the result that during the experiments the methacrylic acid content in the scraper-type cooler constantly fell. This was compensated by a continuous drop in the temperature of the scraper-type cooler to about 6° C. in order to permit a constant formation of crystals on account of the drop in the equilibrium temperature. After ca. 4 hours' operation the liquid phase in the crystalliser (=filtrate from the wash column) had the composition according to Table 6.

TABLE 6

| Name | | Filtrate |
|---|---|---|
| Colour No. | — | >700 |
| Water | % | 5.5 |
| Hydroxyisobutyric acid | % | 2.2 |
| Methacrylamide | % | 1.00 |
| Methyl methacrylate | % | 0.32 |
| Methacrylic acid | % | 89.2 |
| Acetic acid | % | 0.3 |
| Isobutyric acid | % | <0.01 |
| Acrylic acid | % | <0.01 |
| Propionic acid | % | 0.01 |
| MEHQ | % | 0.0488 |
| HQ | % | 0.0053 |

The crystal suspension withdrawn from the crystalliser was compacted in the wash column to form a compact crystal bed. The upper surface of the crystal bed was scraped off by means of a rotating scraper, pumped round the product circulation as a crystal suspension and was melted by the heat exchanger. Part of the suspension was recycled to the countercurrent wash in the crystal bed. The remaining part was continuously obtained as product. The product analysis of the methacrylic acid that was taken approx. 1 hour later than the sample from Table 6, i.e. ca. 5 hours after the start of the experiment, is given as an example in Table 7 of the product qualities that were achieved.

TABLE 7

| Name | | Product |
|---|---|---|
| Colour No. | — | 53 |
| Water | % | 0.12 |
| Hydroxyisobutyric acid | % | 0.03 |
| Methacrylamide | % | 0.07 |
| Methyl methacrylate | % | 0.01 |
| Methacrylic acid | % | 99.8 |
| Acetic acid | % | 0.02 |
| Isobutyric acid | % | <0.01 |
| Acrylic acid | % | <0.01 |
| Propionic acid | % | <0.01 |
| MEHQ | % | 0.0065 |
| HQ | % | 0.0074 |

As can be seen from Table 4, the process according to the invention enables extremely pure methacrylic acid to be produced. On average 6.5 kg/h were produced.

The concentration data were determined by gas chromatography. The colour number was determined according to the method described in DIN-ISO 6271. Water was determined according to ASTM D 1364 and the inhibitors (MEHQ) were determined according to ASTM D 3125.

The invention claimed is:

1. A continuous process for the purification of acrylic acid, having the formula $CH_2$=CH—COOH, comprising a process stage that comprises the following process steps:
   a) crystallizing the acrylic acid out from a mother liquor by a continuous crystallization method;
   b) separating the crystallized acrylic acid from the mother liquor in a wash column by a continuous operation, wherein a suspension is formed from the crystal bed and a wash melt, wherein the suspension is moved to a heat exchanger;
   c) melting at least part of the suspension from b) in the heat exchanger to form molten acrylic acid; and
   d) recycling at least part of the molten acrylic acid to step a) or to step b) and wherein at least part of molten acrylic acid is continuously removed from the process.

2. The continuous process according to claim 1, wherein the crystallized acrylic acid is washed with the recycled acrylic acid in countercurrent thereto.

3. The continuous process according to claim 1, wherein the separated acrylic acid is purified in a separate purification process.

4. The continuous process according to claim 1, wherein the separated, crystallized acrylic acid from step b) or the mother liquor separated after step b) are at least partially fed to step a).

5. The continuous process according to claim 1, wherein the process comprises at least two process stages, wherein each process stage comprises process steps a) to d) and the melted part of step d) of any one process stage is capable of being at least partially recycled to step a) or to step b) of any one of (i) the one process stage, (ii) any other process stage, or (iii) any combination thereof, wherein at least one of the following features (α1) to (α4) is met:
   (α1) separated acrylic acid from a first process stage is fed at least partially to a second process stage;
   (α2) separated acrylic acid from a first process stage is fed at least partially to a first process stage;
   (α3) mother liquor from a first process stage is fed at least partially to a second process stage;
   (α4) mother liquor from a second process stage is fed at least partially to a first process stage; or any combination of any of the preceding.

6. The continuous process according to claim 1, wherein
   (γ1) acrylic acid from an unpurified crude acrylic acid stream from a process for the production of acrylic acid is crystallized;
   (γ2) the acrylic acid crystals are separated from the mother liquor by means of a wash column, wherein the mother liquor from step (γ2) is at least partially recycled to step (γ1), wherein the crude acrylic acid stream has a purity of <99.5 wt. % of acrylic acid; or any combination of any of the preceding.

7. A continuous process for the purification of acrylic acid, having the formula $CH_2$=CH—COOH, comprising a process stage that comprises the following process steps:
   a) crystallizing acrylic acid out from a mother liquor by a continuous crystallization method;
   b) separating crystallized acrylic acid from the mother liquor in a wash column that permits continuous operation of the process, wherein the crystallized acrylic acid is washed and compacted to form a crystal bed, wherein a suspension is formed from the crystal bed and a wash melt, wherein the suspension is moved to a heat exchanger, and the mother liquor is removed from the wash column;
   c) melting at least part of the suspension from b) to form molten acrylic acid; and
   d) the molten acrylic acid is at least partially recycled to step a) or to step b) wherein at least part of acrylic acid is continuously removed from the process.

* * * * *